(12) United States Patent
Konno et al.

(10) Patent No.: US 10,219,745 B2
(45) Date of Patent: Mar. 5, 2019

(54) SENSOR INCLUDING A PEELABLE INSULATION SHEET

(71) Applicants: Nihon Kohden Corporation, Shinjuku-ku, Tokyo (JP); Shinko Electric Industries Co., Ltd., Nagano-shi, Nagano (JP)

(72) Inventors: Norihito Konno, Tokyo (JP); Yoshihiro Ihara, Nagano (JP); Tomoharu Fujii, Nagano (JP)

(73) Assignees: NIHON KOHDEN CORPORATION, Tokyo (JP); SHINKO ELECTRIC INDUSTRIES CO., LTD., Nagano (JP)

( * ) Notice: Subject to any disclaimer, the term of this patent is extended or adjusted under 35 U.S.C. 154(b) by 314 days.

(21) Appl. No.: 15/219,714

(22) Filed: Jul. 26, 2016

(65) Prior Publication Data

US 2017/0027516 A1    Feb. 2, 2017

(30) Foreign Application Priority Data

Jul. 29, 2015    (JP) ................................. 2015-149856

(51) Int. Cl.
*A61B 5/00*    (2006.01)
*A61B 5/0205*    (2006.01)
(Continued)

(52) U.S. Cl.
CPC .......... *A61B 5/6833* (2013.01); *A61B 5/0002* (2013.01); *A61B 5/01* (2013.01);
(Continued)

(58) Field of Classification Search
CPC ..... A61B 5/0002; A61B 5/01; A61B 5/02055; A61B 5/02438; A61B 5/053;
(Continued)

(56) References Cited

U.S. PATENT DOCUMENTS 9,693,732 B1 *    7/2017    Tarler ................... A61B 5/0006
2004/0059212 A1 *    3/2004    Abreu ...................... A61B 5/01
600/373

(Continued)

FOREIGN PATENT DOCUMENTS

JP    2004-529709 A    9/2004
WO    02/089667 A1    11/2002

*Primary Examiner* — Michael Carey
(74) *Attorney, Agent, or Firm* — Pearne & Gordon LLP

(57) ABSTRACT

A sensor includes: a base layer; first and second conduction paths supported by the base layer; a first adhesive layer covering a first portion of the first conduction path; a second adhesive layer covering the second conduction path; an insulation sheet including: a first protecting portion covering the second adhesive layer; a second protecting portion disposed between a second portion of the first conduction path, and a part of the second conduction path; and a third protecting portion covering the first adhesive layer; a detecting section; a wireless transmitter; and a power source. When the insulation sheet is peeled off, the second portion of the first conduction path, and the part of the second conduction path are caused to be in contact with each other, and an electric power is supplied from the power source to the detecting section and the wireless transmitter.

18 Claims, 4 Drawing Sheets

(51) Int. Cl.
*A61B 5/01* (2006.01)
*A61B 5/024* (2006.01)
*A61B 5/053* (2006.01)
*A61B 5/145* (2006.01)
*A61B 5/1455* (2006.01)

(52) U.S. Cl.
CPC ....... *A61B 5/02055* (2013.01); *A61B 5/02438* (2013.01); *A61B 5/053* (2013.01); *A61B 5/14532* (2013.01); *A61B 5/14542* (2013.01); *A61B 5/14551* (2013.01); *A61B 2562/164* (2013.01)

(58) Field of Classification Search
CPC ............ A61B 5/14532; A61B 5/14542; A61B 5/14551; A61B 5/6833; A61B 2562/164
USPC ................................................ 600/300, 301
See application file for complete search history.

(56) References Cited

U.S. PATENT DOCUMENTS

| | | | |
|---|---|---|---|
| 2006/0155183 A1 | 7/2006 | Kroecker | |
| 2011/0237922 A1 | 9/2011 | Parker, III | |
| 2011/0237924 A1 | 9/2011 | McGusty | |
| 2015/0351689 A1* | 12/2015 | Adams | A61B 5/6833 600/300 |
| 2016/0166149 A1* | 6/2016 | Bowers | A61B 5/0006 600/301 |

* cited by examiner

SENSOR INCLUDING A PEELABLE INSULATION SHEET

CROSS-REFERENCE TO RELATED APPLICATION(S)

This application is based upon and claims the benefit of priority from prior Japanese patent application No. 2015-149856, filed on Jul. 29, 2015, the entire contents of which are incorporated herein by reference.

BACKGROUND

The presently disclosed subject matter relates to a sensor which is to be attached to the body of a subject, and which wirelessly transmits a signal corresponding to vital signs information of the subject.

JP-T-2004-529709 discloses a sensor of this kind. The sensor includes a detecting section which detects an electrical signal corresponding to vital signs information of a subject. The electrical signal detected by the detecting section is subjected to a predetermined signal process in a signal processing section, and then wirelessly transmitted to an external medical apparatus through a transmitter.

The sensor includes a power source. The power source is configured so as to supply electric power to the detecting section, the signal processing section, the transmitter, etc. In order to avoid power consumption during non-use of the sensor, a switch device for enabling the power supply from the power source to be performed only during use of the sensor is disposed.

The necessity for providing a switch device causes thickness and size reductions which are requested to be provided in a sensor of this kind, to be inhibited.

SUMMARY

The presently disclosed subject matter may provide a technique which can prevent the size of a sensor from being increased, while avoiding power consumption during non-use of the sensor.

The sensor, which is adapted to be attached to a body of a subject, may comprise: a base layer; a first conduction path which is supported by the base layer; a first adhesive layer which is supported by the base layer, and which is configured to cover a first portion of the first conduction path; a second conduction path which is supported by the base layer; a second adhesive layer which is supported by the base layer, and which is configured to cover the second conduction path; an insulation sheet including: a first protecting portion which is configured to peelably cover the second adhesive layer; a second protecting portion which is peelably disposed between a second portion of the first conduction path, and a part of the second conduction path; and a third protecting portion which is configured to peelably cover the first adhesive layer; a detecting section which is supported by the base layer so as to be electrically connected to one of the first conduction path and the second conduction path, and which is configured to detect vital signs information of the subject; a wireless transmitter which is supported by the base layer so as to be electrically connected to the one of the first conduction path and the second conduction path, and which is configured to wirelessly transmit the vital signs information to an external apparatus; and a power source which is supported by the base layer so as to be electrically connected to the other of the first conduction path and the second conduction path, wherein, when the insulation sheet is peeled off, the second portion of the first conduction path, and the part of the second conduction path are caused to be in contact with each other, and an electric power is supplied from the power source to the detecting section and the wireless transmitter.

DETAILED DESCRIPTION OF EXEMPLARY EMBODIMENTS

Figure 1:
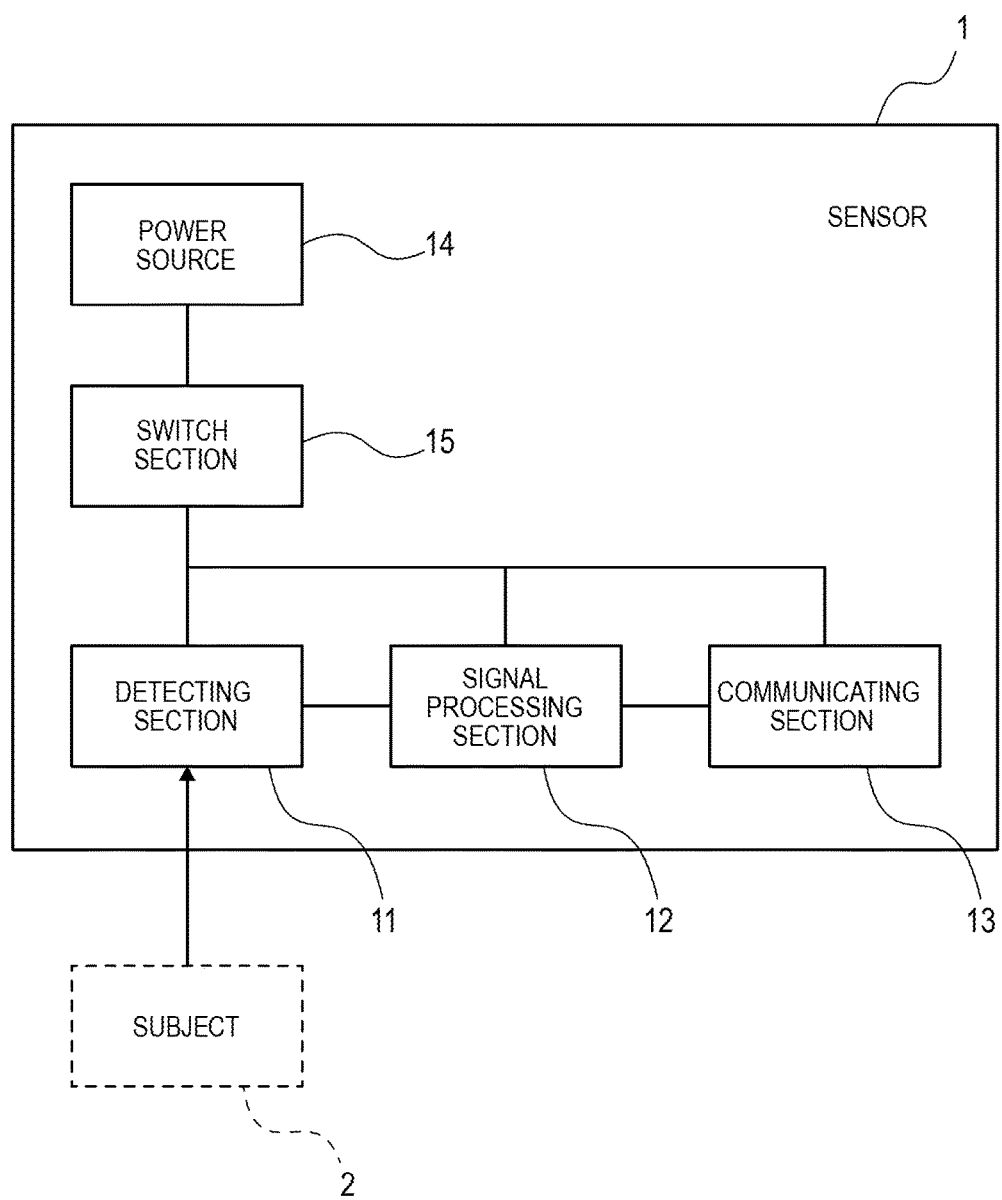
FIG. 1 is a view illustrating the functional configuration of a sensor of a first embodiment.
Figure 2A:
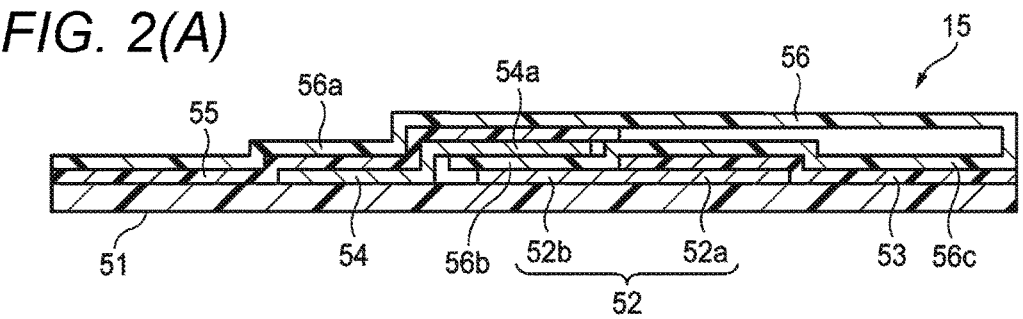
FIGS. 2 (A) to 2 (D) are views illustrating the configuration of a switch section of the sensor of the first embodiment.
Figure 2B:
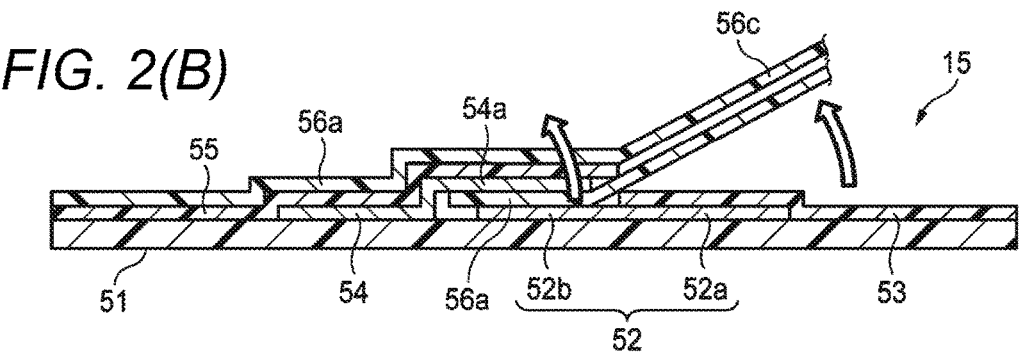
Figure 2C:
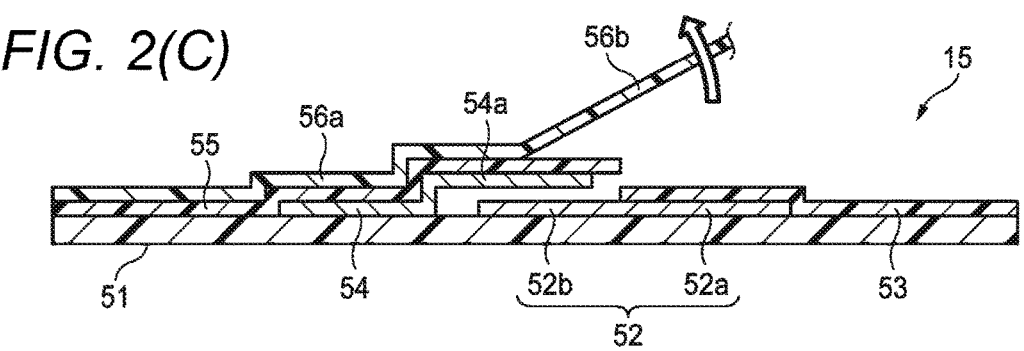
Figure 2D:
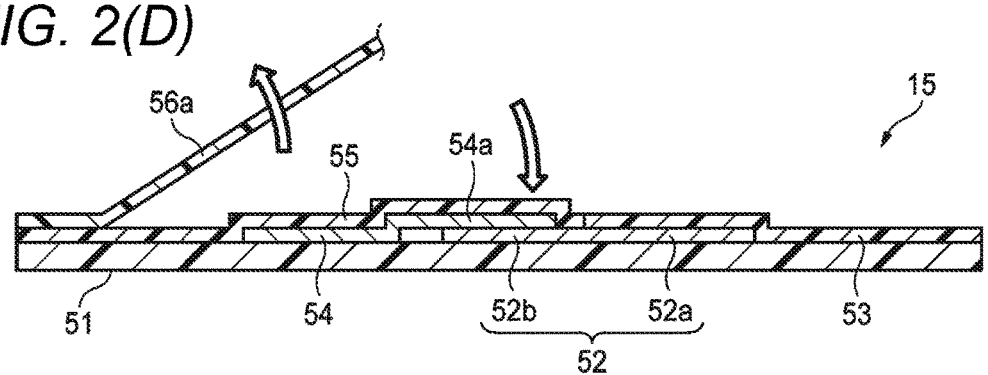
Figure 3A:
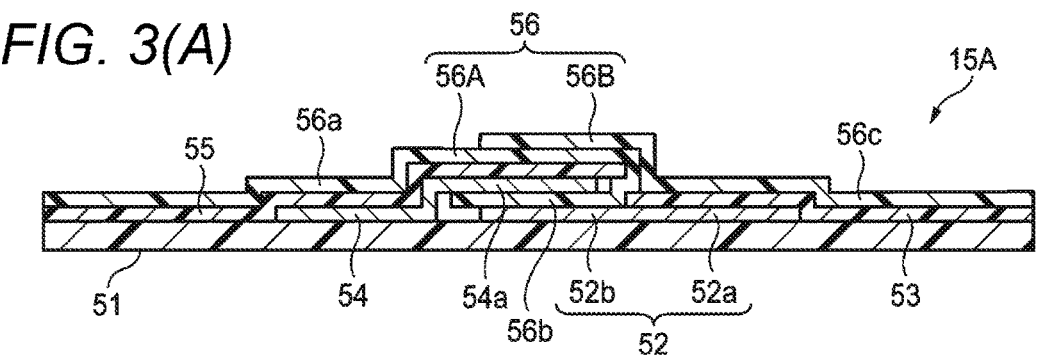
FIGS. 3 (A) to 3 (D) are views illustrating the configuration of a switch section of a sensor of a second embodiment.
Figure 3B:
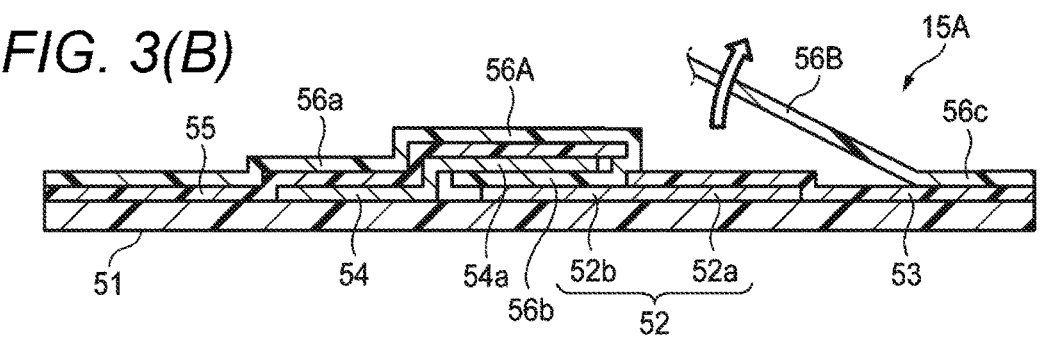
Figure 3C:
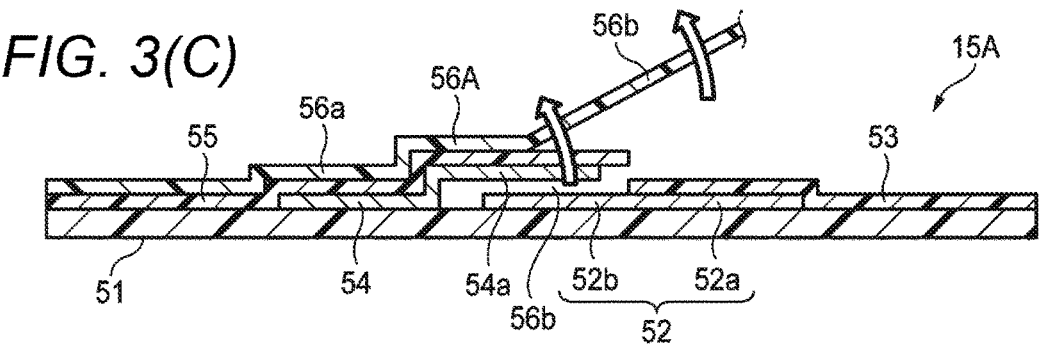
Figure 3D:
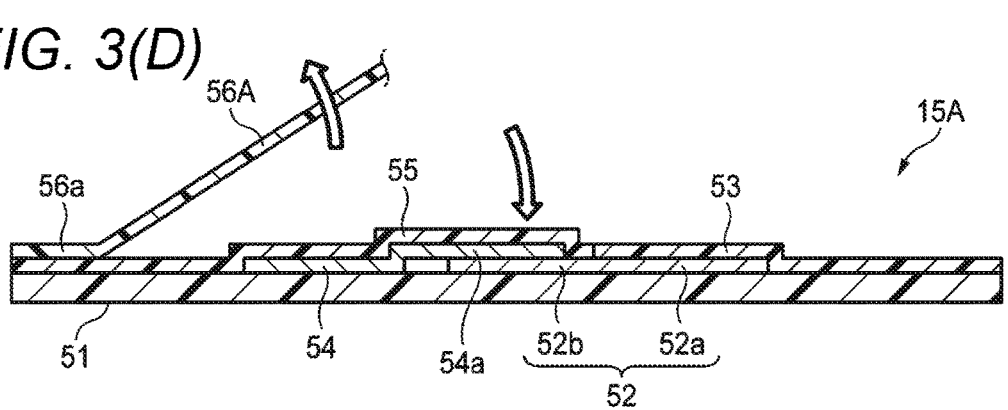
Figure 4A:
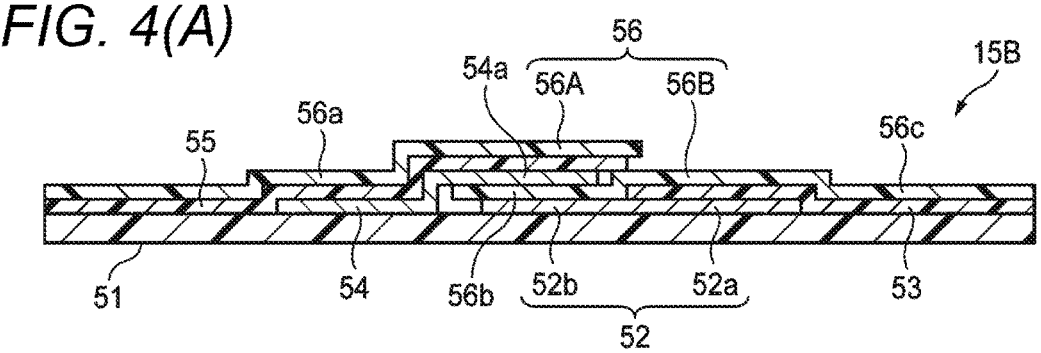
FIGS. 4 (A) to 4 (D) are views illustrating the configuration of a switch section of a sensor of a third embodiment.
Figure 4B:
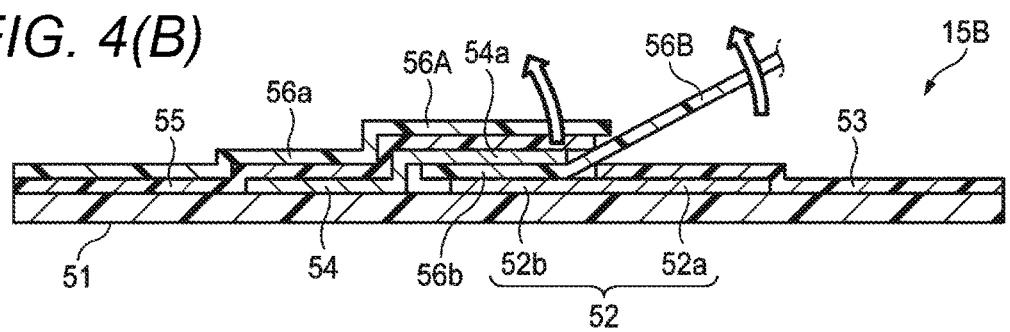
Figure 4C:
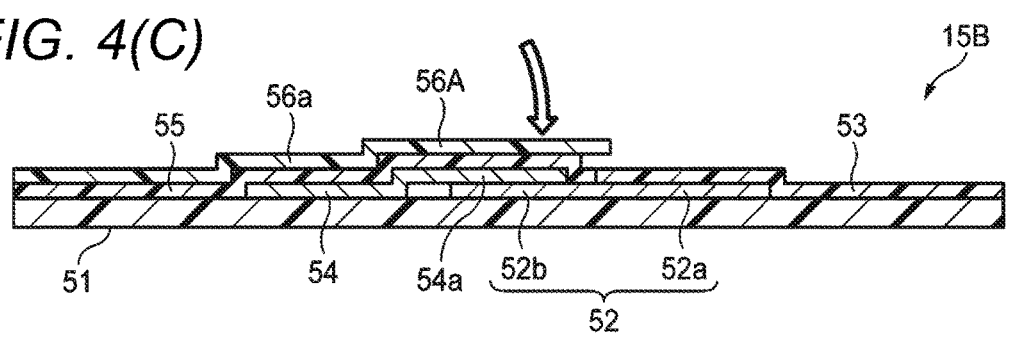
Figure 4D:
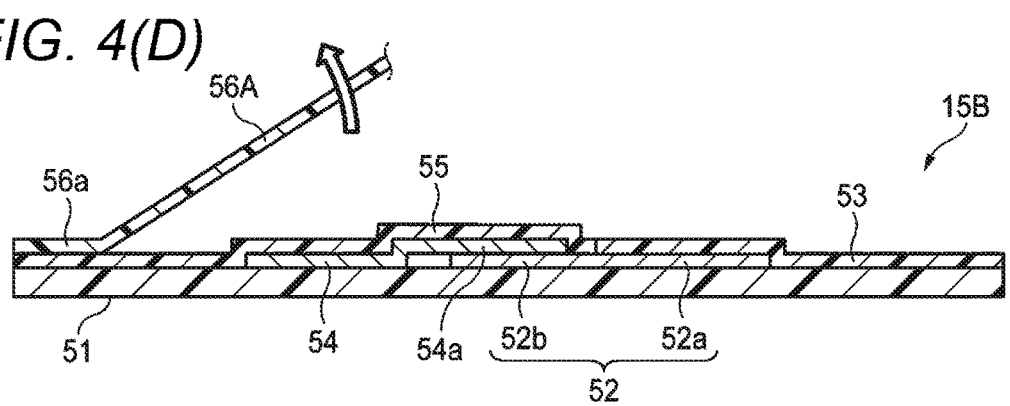

Embodiments will be described in detail with reference to the accompanying drawings. In the drawings described in the specification, in order to make the components to have a recognizable size, their scales are appropriately changed.

FIG. 1 diagrammatically illustrates the functional configuration of a sensor 1 of a first embodiment. The sensor 1 is configured so as to be attached to the body of a subject 2 to acquire vital signs information of the subject 2. Examples of vital signs information are the biopotential, the body temperature, the pulse rate, the arterial oxygen saturation, and the blood glucose level. The biopotential may be a value indicating a change of the potential of vital signs information, and includes the electrocardiogram, the impedance respiration, the thermistor respiration, the heart rate, the cardiac output, and the like.

The sensor 1 may include a detecting section 11. The detecting section 11 detects vital signs information of the subject 2, and outputs a signal corresponding to the vital signs information.

The detecting section 11 may have various modes in accordance with vital signs information to be acquired. In the case where the electrocardiogram or the impedance respiration is to be acquired as vital signs information, the detecting section 11 has a mode which is configured by a plurality of electrodes for detecting the biopotential. In the case where the thermistor respiration or the body temperature is to be acquired as vital signs information, the detecting section 11 has a mode which is configured by a temperature detecting device. In the case where the pulse rate or the arterial oxygen saturation is to be acquired as vital signs information, the detecting section 11 has a mode which is configured by a light emitter and a light receiver. The light emitter emits a light beam of a predetermined wavelength, and the light receiver is configured so as to have sensitivity to a light beam of the wavelength. In the case where the blood glucose level is to be acquired as vital signs information, the detecting section 11 has a mode which is configured by a blood glucose sensing device.

The sensor 1 may include a signal processing section 12. The signal processing section 12 is electrically connected to the detecting section 11. The signal processing section 12 may include a signal amplifier, an A/D converter, a central processing unit, and the like. The signal processing section 12 performs predetermined signal processing on the signal which is output from the detecting section 11. For example, an analog signal which is output from the detecting section 11, and which corresponds to the signal is amplified, and then converted to a digital signal. The central processing unit generally controls the operations of the devices included in the signal processing section 12.

The sensor 1 may include a communicating section 13. The communicating section 13 is electrically connected to the signal processing section 12. The communicating section 13 may include an antenna for communicating with an external apparatus by using a predetermined wireless communication method. Examples of the wireless communication method are BLE (Bluetooth Low Energy (Bluetooth is a registered trademark)), ZigBee (registered trademark), ANT+ (registered trademark), NFC (registered trademark), and WiFi (registered trademark). The communicating section 13 (an example of the wireless transmitter) wirelessly transmits the signal which is detected by the detecting section 11, and which is signal-processed by the signal processing section 12, to the external apparatus. Namely, the communicating section 13 wirelessly transmits the vital signs information of the subject 2. The communicating section 13 may wirelessly receive a predetermined control signal.

The sensor 1 may include a power source 14. The power source 14 supplies electric power which is necessary for operating the detecting section 11, the signal processing section 12, and the communicating section 13.

The sensor 1 may include a switch section 15. The switch section 15 is configured so as to take either of first and second states. In the first state, the power source 14 is electrically insulated from the detecting section 11, the signal processing section 12, and the communicating section 13. In the second state, the power source 14 is electrically connected to the detecting section 11, the signal processing section 12, and the communicating section 13.

During non-use of the sensor 1, namely, the switch section 15 takes the first state, and, during use of the sensor 1, takes the second state. According to the configuration, it is possible to avoid power consumption during non-use of the sensor 1.

FIG. 2 (A) shows a sectional configuration of the switch section 15 in the embodiment. The switch section 15 may include a base layer 51. The base layer 51 is formed by an appropriate material having electrical insulation properties. Although not illustrated, the base layer 51 supports the detecting section 11, the signal processing section 12, the communicating section 13, and the power source 14.

The switch section 15 may include a first conduction path 52. The first conduction path 52 is supported by the base layer 51. The first conduction path 52 is electrically connected to the power source 14.

The switch section 15 may include a first adhesive layer 53. The first adhesive layer 53 is formed by an appropriate material having adhesive and electrical insulation properties. The first adhesive layer 53 is supported by the base layer 51. The first adhesive layer 53 covers a first portion 52a of the first conduction path 52.

The switch section 15 may include a second conduction path 54. The second conduction path 54 is supported by the base layer 51. The second conduction path 54 is electrically connected to the detecting section 11, the signal processing section 12, and the communicating section 13. An end portion 54a (an example of the part of the second conduction path) of the second conduction path 54 is extended over a second portion 52b of the first conduction path 52 so as to be overlapped with the second portion 52b.

The switch section 15 may include a second adhesive layer 55. The second adhesive layer 55 is formed by an appropriate material having adhesive and electrical insulation properties. The second adhesive layer 55 is supported by the base layer 51. The second adhesive layer 55 covers the second conduction path 54.

During non-use of the sensor 1, the switch section 15 includes an insulation sheet 56. The insulation sheet 56 is formed by an appropriate material having electrical insulation properties. The insulation sheet 56 itself is not adhesive, and is formed by an appropriate material having peelable properties to the material forming the first adhesive layer 53 and that forming the second adhesive layer 55.

The insulation sheet 56 has a first protecting portion 56a, a second protecting portion 56b, and a third protecting portion 56c. The first protecting portion 56a peelably covers the second adhesive layer 55. The second protecting portion 56b is peelably disposed between the second portion 52b of the first conduction path 52, and the end portion 54a of the second conduction path 54. The third protecting portion 56c peelably covers the first adhesive layer 53.

In the state illustrated in FIG. 2 (A), namely, the first conduction path 52 and the second conduction path 54 are electrically insulated from each other by the insulation sheet 56. Therefore, the switch section 15 takes the above-described first state.

During use of the sensor 1, as illustrated in FIG. 2 (B), first, the third protecting portion 56c of the insulation sheet 56 is peeled from the first adhesive layer 53. Then, the end portion 54a of the second conduction path 54 is lifted, and, as illustrated in FIG. 2 (C), the second protecting portion 56b of the insulation sheet 56 is peeled from between the second portion 52b of the first conduction path 52, and the end portion 54a of the second conduction path 54. As illustrated in FIG. 2 (D), finally, the first protecting portion 56a of the insulation sheet 56 is peeled from the second adhesive layer 55.

As a result of peeling of the insulation sheet 56, the second portion 52b of the first conduction path 52, and the end portion 54a of the second conduction path 54 are mechanically made in contact with each other. This causes the first conduction path 52 and the second conduction path 54 to be electrically connected to each other, and the power source 14 to be electrically connected to the detecting section 11, the signal processing section 12, and the communicating section 13. Namely, the switch section 15 takes the above-described second state. The power source 14 starts the power supply to the detecting section 11, the signal processing section 12, and the communicating section 13. The detecting section 11, the signal processing section 12, and the communicating section 13 start the respective predetermined operations by using the electric power.

On the other hand, the removal of the insulation sheet 56 causes the first adhesive layer 53 and the second adhesive layer 55 to be exposed. This enables the sensor 1 to be attached to the body of the subject 2 through the first adhesive layer 53 and the second adhesive layer 55.

According to the configuration, during non-use of the sensor 1, the insulation sheet 56 functions not only as a protection sheet which prevents the first and second adhesive layers 53, 55 from being adhered to the body of the subject 2, but also as an insulator which electrically insulates the power source 14 from the detecting section 11, the signal processing section 12, and the communicating section 13. During use of the sensor 1, simply by peeling off the insulation sheet 56, the first and second adhesive layers 53, 55 are exposed in a manner that the layers can be adhered to the body of the subject 2, and the power source 14 is electrically connected to the detecting section 11, the signal processing section 12, and the communicating section 13. Namely, the insulation sheet 56 protects the first and second adhesive layers 53, 55, and functions as a switch for switching the electrical connection states of the power source 14 to the detecting section 11, the signal processing section 12, and the communicating section 13.

Therefore, there is no necessity for providing a switch in order to avoid power consumption during non-use of the sensor 1. Moreover, the insulation sheet 56 itself is very thin, and the areas for covering the first and second adhesive layers 53, 55 are originally necessary. Therefore, it is possible to prevent the size of the sensor 1 from being increased, while avoiding power consumption during non-use of the sensor 1 at a low cost.

Preferably, the base layer 51 is flexible. In this case, when the first and second adhesive layers 53, 55 are to be attached to the body of the subject 2, the base layer 51 can flex along the shape of the body of the subject 2. Therefore, the attachment properties of the sensor 1 to the body of the subject 2 can be improved.

FIG. 3 (A) illustrates a sectional configuration of a switch section 15A of the sensor 1 of a second embodiment. The components which are identical with or equivalent to those of the switch section 15 in the first embodiment are denoted by the same reference numerals, and their duplicate description will be omitted.

In the embodiment, the insulation sheet 56 includes a first insulation sheet 56A and a second insulation sheet 56B. The first insulation sheet 56A has the above-described first and second protecting portions 56a, 56b. The second insulation sheet 56B has the above-described third protecting portion 56c.

In the state illustrated in FIG. 3 (A), namely, the first conduction path 52 and the second conduction path 54 are electrically insulated from each other by the first insulation sheet 56A. Therefore, the switch section 15A takes the above-described first state.

During use of the sensor 1, as illustrated in FIG. 3 (B), first, the third protecting portion 56c of the second insulation sheet 56B is peeled from the first adhesive layer 53. As illustrated in FIG. 3 (C), then, the second protecting portion 56b of the first insulation sheet 56A is peeled from between the second portion 52b of the first conduction path 52, and the end portion 54a of the second conduction path 54. The end portion 54a of the second conduction path 54 is lifted. As illustrated in FIG. 3 (D), finally, the first protecting portion 56a of the first insulation sheet 56A is peeled from the second adhesive layer 55.

As a result of peeling of the first insulation sheet 56A and the second insulation sheet 56B, the second portion 52b of the first conduction path 52, and the end portion 54a of the second conduction path 54 are mechanically made in contact with each other. This causes the first conduction path 52 and the second conduction path 54 to be electrically connected to each other, and the power source 14 to be electrically connected to the detecting section 11, the signal processing section 12, and the communicating section 13. Namely, the switch section 15A takes the above-described second state. The power source 14 starts the power supply to the detecting section 11, the signal processing section 12, and the communicating section 13. The detecting section 11, the signal processing section 12, and the communicating section 13 start the respective predetermined operations by using the electric power.

On the other hand, the removal of the first insulation sheet 56A and the second insulation sheet 56B causes the first adhesive layer 53 and the second adhesive layer 55 to be exposed. This enables the sensor 1 to be attached to the body of the subject 2 through the first adhesive layer 53 and the second adhesive layer 55.

Also in the configuration, there is no necessity for providing a switch in order to avoid power consumption during non-use of the sensor 1. Moreover, the first and second insulation sheets 56A, 56B themselves are very thin, and the areas for covering the first and second adhesive layers 53, 55 are originally necessary. Therefore, it is possible to prevent the size of the sensor 1 from being increased, while avoiding power consumption during non-use of the sensor 1 at a low cost.

FIG. 4 (A) shows a sectional configuration of a switch section 15B of the sensor 1 of a third embodiment. The components which are identical with or equivalent to those of the switch section 15 in the first embodiment are denoted by the same reference numerals, and their duplicate description will be omitted.

In the embodiment, the insulation sheet 56 includes the first insulation sheet 56A and the second insulation sheet 56B. The first insulation sheet 56A has the above-described first protecting portion 56a. The second insulation sheet 56B has the above-described second and third protecting portions 56b, 56c.

In the state illustrated in FIG. 4 (A), namely, the first conduction path 52 and the second conduction path 54 are electrically insulated from each other by the second insulation sheet 56B. Therefore, the switch section 15B takes the above-described first state.

During use of the sensor 1, as illustrated in FIG. 4 (B), first, the third protecting portion 56c of the second insulation sheet 56B is peeled from the first adhesive layer 53. Then, the end portion 54a of the second conduction path 54 is lifted, and, as illustrated in FIG. 4 (C), the second protecting portion 56b of the second insulation sheet 56B is peeled from between the second portion 52b of the first conduction path 52, and the end portion 54a of the second conduction path 54. As illustrated in FIG. 4 (D), finally, the first protecting portion 56a of the first insulation sheet 56A is peeled from the second adhesive layer 55.

As a result of peeling of the first insulation sheet 56A and the second insulation sheet 56B, the second portion 52b of the first conduction path 52, and the end portion 54a of the second conduction path 54 are mechanically made in contact with each other. This causes the first conduction path 52 and the second conduction path 54 to be electrically connected to each other, and the power source 14 to be electrically connected to the detecting section 11, the signal processing section 12, and the communicating section 13. Namely, the switch section 15B takes the above-described second state. The power source 14 starts the power supply to the detecting section 11, the signal processing section 12, and the communicating section 13. The detecting section 11, the signal processing section 12, and the communicating section 13 start the respective predetermined operations by using the electric power.

On the other hand, the removal of the first insulation sheet 56A and the second insulation sheet 56B causes the first adhesive layer 53 and the second adhesive layer 55 to be exposed. This enables the sensor 1 to be attached to the body of the subject 2 through the first adhesive layer 53 and the second adhesive layer 55.

Also in the configuration, there is no necessity for providing a switch in order to avoid power consumption during non-use of the sensor 1. Moreover, the first and second insulation sheets 56A, 56B themselves are very thin, and the areas for covering the first and second adhesive layers 53, 55 are originally necessary. Therefore, it is possible to prevent the size of the sensor 1 from being increased, while avoiding power consumption during non-use of the sensor 1 at a low cost.

The foregoing description of the embodiments has been made in order to facilitate understanding of the presently disclosed subject matter, and is not intended to limit the presently disclosed subject matter. It is a matter of course that the presently disclosed subject matter may be chanced or improved without departing the spirit thereof, and includes equivalents thereof.

In the embodiments, the first conduction path 52 is electrically connected to the power source 14, and the second conduction path 54 is electrically connected to the detecting section 11, the signal processing section 12, and the communicating section 1. Alternatively, the second conduction path 54 may be electrically connected to the power source 14, and the first conduction path 52 maybe electrically connected to the detecting section 11, the signal processing section 12, and the communicating section 13.

The arrangement of the detecting section 11, the signal processing section 12, the communicating section 13, and the power source 14 on the base layer 51 may be adequately determined in accordance with the specification of the sensor 1. The arrangement of the first conduction path 52, the first adhesive layer 53, the second conduction path 54, the second adhesive layer 55, and the insulation sheet 56 with respect to the base layer 51, and the shapes of the components are not limited to those of the embodiments illustrated in FIGS. 2 (A) to 4 (D), and may be adequately determined in accordance with the specification of the sensor 1.

According to an aspect of the presently disclosed subject matter, during non-use of the sensor, the insulation sheet functions not only as a protection sheet which prevents the first and second adhesive layers from being adhered to the body of the subject, but also as an insulator which electrically insulates the power source from the detecting section and the wireless transmitter. During use of the sensor, simply by peeling off the insulation sheet, the first and second adhesive layers are exposed in a manner that the layers can be adhered to the body of the subject, and the power source is electrically connected to the detecting section and the wireless transmitter. Namely, the insulation sheet functions as a protection sheet which protects the first and second adhesive layers, and also as a switch for switching the electrical connection states of the power source to the detecting section and the wireless transmitter.

Therefore, there is no necessity for providing a switch in order to avoid power consumption during non-use of the sensor. Moreover, the insulation sheet itself is very thin, and the areas for covering the first and second adhesive layers are originally necessary. Therefore, it is possible to prevent the size of the sensor from being increased, while avoiding power consumption during non-use of the sensor at a low cost.

What is claimed is:

1. A sensor which is adapted to be attached to a body of a subject, the sensor comprising:
    a base layer;
    a first conduction path which is supported by the base layer;
    a first adhesive layer which is supported by the base layer, and which is configured to cover a first portion of the first conduction path;
    a second conduction path which is supported by the base layer;
    a second adhesive layer which is supported by the base layer, and which is configured to cover the second conduction path;
    an insulation sheet including: a first protecting portion which is configured to peelably cover the second adhesive layer; a second protecting portion which is peelably disposed between a second portion of the first conduction path, and a part of the second conduction path; and a third protecting portion which is configured to peelably cover the first adhesive layer;
    a detecting section which is supported by the base layer so as to be electrically connected to one of the first conduction path and the second conduction path, and which is configured to detect vital signs information of the subject;
    a wireless transmitter which is supported by the base layer so as to be electrically connected to the one of the first conduction path and the second conduction path, and which is configured to wirelessly transmit the vital signs information to an external apparatus; and
    a power source which is supported by the base layer so as to be electrically connected to the other of the first conduction path and the second conduction path, wherein,
    when the insulation sheet is peeled off, the second portion of the first conduction path, and the part of the second conduction path are caused to be in contact with each other, and an electric power is supplied from the power source to the detecting section and the wireless transmitter.

2. The sensor according to claim 1, wherein
    the insulation sheet includes: a first insulation sheet which has the first protecting portion and the second protecting portion; and a second insulation sheet which has the third protecting portion, and,
    when the first insulation sheet and the second insulation sheet are peeled off, the second portion of the first conduction path, and the part of the second conduction path are caused to be in contact with each other, and an electric power is supplied from the power source to the detecting section and the wireless transmitter.

3. The sensor according to claim 1, wherein
    the insulation sheet includes: a first insulation sheet which has the first protecting portion; and a second insulation sheet which has the second protecting portion and the third protecting portion, and,
    when the first insulation sheet and the second insulation sheet are peeled off, the second portion of the first conduction path, and the part of the second conduction path are caused to be in contact with each other, and an electric power is supplied from the power source to the detecting section and the wireless transmitter.

4. The sensor according to claim 1, wherein
    the base layer is flexible.

5. The sensor according to claim 1, wherein
    the detecting section detects, as the vital signs information, at least one of a biopotential, a body temperature, a pulse rate, an arterial oxygen saturation, and a blood glucose level.

6. The sensor according to claim 1, wherein
the part of the second conduction path is extended over the second portion of the first conduction path so as to be overlapped with the second portion.

7. A sensor which is adapted to be attached to a body of a subject, the sensor comprising:
 a base layer;
 a first electrical component;
 a second electrical component; and
 a switch section for electrically connecting the first electrical component to the second electrical component, the switch section comprising:
  a first conduction path supported by the base layer, the first conduction path being electrically connected to the first electrical component,
  a second conduction path supported by the base layer, the second conduction path being electrically connected to the second electrical component, and
  an insulation sheet having an insulating portion peelably disposed between a contact portion of the first conduction path and a contact portion of the second conduction path so as to insulate the contact portion of the first conduction path from the contact portion of the second conduction path such that the first electrical component and second electrical component are electrically insulated from each other,
 wherein when the insulation sheet is peeled off, the contact portion of the first conduction path and the contact portion of the second conduction path are caused to be in electrical contact with each other such that the first electrical component and second electrical component are electrically connected to each other.

8. The sensor according to claim 7, wherein:
 the first electrical component comprises a power source,
 the second electrical component comprises a detecting section configured to detect vital signs information of the subject, and
 when the insulation sheet is peeled off, the contact portion of the first conduction path and the contact portion of the second conduction path are caused to be in electrical contact with each other such that an electric power is supplied from the power source to the detecting section.

9. The sensor according to claim 8, wherein the detecting section detects at least one vital sign from a group consisting a biopotential, a body temperature, a pulse rate, an arterial oxygen saturation, and a blood glucose level.

10. The sensor according to claim 8, wherein:
 the second electrical component further comprises a signal processing section configured to process a signal output from the detecting section, and
 when the insulation sheet is peeled off, the contact portion of the first conduction path and the contact portion of the second conduction path are caused to be in electrical contact with each other such that an electric power is supplied from the power source to the signal processing section.

11. The sensor according to claim 10, wherein the signal processing section comprises at least one member from a group consisting of a signal amplifier, an A/D converter, and a central processing unit.

12. The sensor according to claim 8, wherein:
 the second electrical component further comprises a wireless transmitter configured to wirelessly transmit the vital signs information to an external apparatus, and
 when the insulation sheet is peeled off, the contact portion of the first conduction path and the contact portion of the second conduction path are caused to be in electrical contact with each other such that an electric power is supplied from the power source to the wireless transmitter.

13. The sensor according to claim , wherein
the contact portion of the second conduction path is extended over the contact portion of the first conduction path so as to be overlapped with the contact portion of the first conduction path.

14. The sensor according to claim 7, further comprising:
 a first adhesive layer supported by the base layer that at least partially covers the first conductive path; and
 a second adhesive layer supported by the base layer that at least partially covers the second conductive path,
 wherein the insulation sheet includes a first protecting portion that peelably covers the first adhesive layer and a second protecting portion that peelably covers the second adhesive layer.

15. The sensor according to claim 14, wherein the insulation sheet includes: a first insulation sheet that defines the first protecting portion, and a second insulation sheet that defines the insulating portion and second protecting portion.

16. The sensor according to claim 14, wherein the insulation sheet includes:
 a first insulation sheet that defines the first protecting portion and the insulating portion, and
 a second insulation sheet that defines the second protecting portion.

17. The sensor according to claim 7, wherein the base layer is flexible.

18. The sensor according to claim 7, wherein the first electrical component and the second electrical component are supported by the base layer.

* * * * *

UNITED STATES PATENT AND TRADEMARK OFFICE
CERTIFICATE OF CORRECTION

PATENT NO. : 10,219,745 B2
APPLICATION NO. : 15/219714
DATED : March 5, 2019
INVENTOR(S) : Norihito Konno et al.

It is certified that error appears in the above-identified patent and that said Letters Patent is hereby corrected as shown below:

In the Specification

Column 1, Line 44, "laver" should be -- layer --.

Column 1, Line 56, "laver" should be -- layer --.

Column 6, Line 53, "15B" should be -- 15A --.

Column 7, Line 3, "lavers" should be -- layers --.

Column 7, Line 12, "chanced" should be -- changed --.

Column 7, Line 19, "1" should be -- 13 --.

Signed and Sealed this
Second Day of July, 2019

Andrei Iancu
*Director of the United States Patent and Trademark Office*